United States Patent [19]

Kysela et al.

[11] Patent Number: 4,755,621

[45] Date of Patent: Jul. 5, 1988

[54] PROCESS FOR THE PREPARATION OF 2,3,5,6-TETRAFLUOROBENZOIC ACID, AND THE NEW COMPOUNDS 2,3,5,6-TETRACHLORO-4-TRIFLUOROMETHYL-BENZOYL CHLORIDE AND 2,3,5,6-TETRAFLUORO-4-TRIFLUOROMETHYL-BENZOYL FLUORIDE

[75] Inventors: Ernst Kysela, Bergisch Gladbach; Rudolf Braden, Odenthal, both of Fed. Rep. of Germany

[73] Assignee: Bayer Aktiengesellschaft, Leverkusen, Fed. Rep. of Germany

[21] Appl. No.: 61,941

[22] Filed: Jun. 11, 1987

[30] Foreign Application Priority Data

Jun. 28, 1986 [DE] Fed. Rep. of Germany ....... 3621707

[51] Int. Cl.$^4$ ............................................ C07C 51/255
[52] U.S. Cl. ............................... 562/411; 260/544 F; 260/544 D
[58] Field of Search ................... 562/411; 260/544 F, 260/544 D

[56] References Cited

U.S. PATENT DOCUMENTS 3,459,794  8/1969  Tamborski .

FOREIGN PATENT DOCUMENTS 2146635  4/1985  United Kingdom .

OTHER PUBLICATIONS

Kobrina, L. S. et al, Izv. Sib. Otd. Akad. Nauk SSSR Ser. Khim. Nauk (2) 91–9, 1986.
Gerasimova, T. et al, Izv. Sib. Otd. Akad. Nauk SSSR, Ser. Khim Nauk (5) 100–6, 1975.
R. J. Harper, Jr., E. J. Soloski and C. Tamborski, *J. Org. Chem.*, 29, 2385–2389 (1964).
V. I. Vysochin, V. A. Barkhash and N. N. Vorozhtsov, *Zh. Obsh. Chim.*, 39, 1607–1615 (1969).
G. G. Yakobson, G. G. Furin and T. V. Terent'eva, *Zh. Org. Khim.*, 10, 799–804 (1974).
D. J. Alsop, J. Burdon and J. C. Tatlow, *J. Chem. Soc.*, 1801–1805 (1962).

*Primary Examiner*—Paul J. Killos
*Attorney, Agent, or Firm*—Sprung Horn Kramer & Woods

[57] ABSTRACT

2,3,5,6-Tetrafluorobenzoic acid is prepared from 4-trifluoromethyl-benzoyl fluoride by chlorination, fluorination, hydrolysis, decarboxylation and saponification. The new compounds 2,3,5,6-tetrachloro-4-trifluoromethyl-benzoyl chloride and 2,3,5,6-tetrafluoro-4-trifluoromethyl-benzoyl fluoride are produced during this as intermediates.

20 Claims, No Drawings

PROCESS FOR THE PREPARATION OF 2,3,5,6-TETRAFLUOROBENZOIC ACID, AND THE NEW COMPOUNDS 2,3,5,6-TETRACHLORO-4-TRIFLUOROMETHYL-BENZOYL CHLORIDE AND 2,3,5,6-TETRAFLUORO-4-TRIFLUOROMETHYL-BENZOYL FLUORIDE

BACKGROUND OF THE INVENTION

Field of the Invention

The present invention relates to a process for the preparation of 2,3,5,6-tetrafluorobenzoic acid from 4-trifluoromethyl-benzoyl fluoride, and to the new compounds 2,3,5,6-tetrachloro-4-trifluoromethyl-benzoyl chloride and 2,3,5,6-tetrafluoro-4-trifluoromethyl-benzoyl fluoride.

BACKGROUND INFORMATION 2,3,5,6-Tetrafluorobenzoic acid is a known compound which can be used, for example, for the preparation of highly effective insecticides (see DE-OS (German Published Specification) 2,658,074). The known processes for the preparation of this compound are afflicted by serious disadvantages, particularly for execution on an industrial scale. For example, they require poorly accessible starting materials, reactions which are difficult to carry out and chemicals which are difficult to handle, and/or they are not very selective (see, for example, R. J. Harper et al., *J. O. C.* 29, 2385-9 (1964)—main disadvantage: Grignard reaction; V. I. Vysocin et al., *Zh. Obsh. Chim.* 39, 1607-15 (1969)—main disadvantage: use of lithium aluminium hydride, G. G. Yakobson et al., *Zh. Org. Khim.*, 10, 799-804 (1974)—main disadvantage: use of antimony(V) fluoride; EP-OS (European Published Specification) No. 60,617—main disadvantage: use of butyllithium, and D. J. Alsop et al., *J. Chem. Soc.*, 1962, 1801-5—main disadvantage: low yield).

SUMMARY OF THE INVENTION

A process has now been found for the preparation of 2,3,5,6-tetrafluorobenzoic acid, which process is characterized in that (a) 4-trifluoromethyl-benzoyl fluoride is chlorinated in the presence of chlorosulphonic acid and, if appropriate, in the presence of a solvent at temperatures of less than 60° C. to form 2,3,5,6-tetrachloro-4-trifluoromethyl-benzoyl chloride (b) 2,3,5,6-tetrachloro-4-trifluoromethyl-benzoyl chloride is fluorinated using potassium fluoride in the presence of an aprotic, dipolar, inert solvent to form 2,3,5,6-tetrafluoro-4-trifluoromethyl-benzoyl fluoride, (c) 2,3,5,6-tetrafluoro-4-trifluoromethyl-benzoyl fluoride is hydrolyzed to form 2,3,5,6-tetrafluoro-4-tetrafluoromethyl-benzoic acid, (d) 2,3,5,6-tetrafluoro-4-trifluoromethyl-benzoic acid is decarboxylated at an elevated temperature to form 2,3,5,6-tetrafluoro-benzotrifluoride, and (e) 2,3,5,6-tetrafluoro-benzotrifluoride is saponified using oleum to form 2,3,5,6-tetrafluoro-benzoic acid.

The products of steps (b) and (c) are preferably not isolated. A procedure is preferably followed in which steps (c) and (d) are allowed to proceed immediately after one another and in the same vessel as step (b) without isolation of the product of step (b), and temperatures are adjusted during or after hydrolysis at which time the decarboxylation occurs. In this fashion, the process according to the invention proceeds as a 3-step reaction.

DETAILED DESCRIPTION OF THE INVENTION

The preferred embodiment of the process according to the invention may be illustrated, for example, by the following equation:

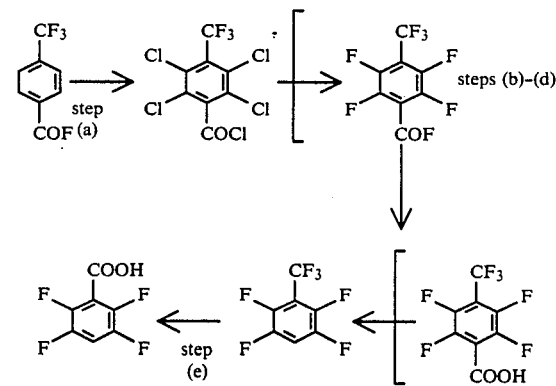

The starting material 4-trifluoromethyl-benzoyl fluoride which is required for step (a) is a commercially available product.

Chlorosulphonic acid may be employed, for example, in amounts from 2 to 10 mol per mol of 4-trifluoromethyl-4-benzoyl fluoride. This amount is preferably 4 - 7.5 mol. The chlorination in step a) may generally be carried out using elemental chlorine.

For example, chlorine may be passed into the reaction mixture as long as it is taken up there. It may be advantageous to add a small amount of iodine to the reaction mixture, for example 0.01-2% by weight relative to the chlorine employed. It may furthermore be advantageous to carry out the chlorination in the presence of a solvent. Suitable solvents are, for example, carbon tetrachloride, tetrachloroethane, difluorotetrachloroethane and sulphuryl chloride. 1,1,2,2-Tetrachloroethane and sulphuryl chloride, of which 100-500% by weight, relative to 4-trifluoromethylbenzoyl fluoride, may be employed, for example, is preferred. Preferred temperatures for the chlorination are, for example, those in the range from 40 to 60° C., particularly those in the range from 40° to 55° C. In principle, the chlorination can also be carried out at temperatures above 60° C., but the yield of the desired chlorination product then decreases considerably.

The reaction mixture present after the chlorination reaction of step a) may be worked up, for example, by introducing it into an ice-water mixture, if appropriate after previous cooling, and separating off the 2,3,5,6-tetrachloro-4-trifluoromethyl-benzoyl chloride with the aid of an organic solvent. This organic solvent may be a solvent which is, if appropriate, already present during the reaction, for example carbon tetrachloride. However, it is also possible not to add the organic solvent until the work-up or to add the solvent additionally during the work-up. A 2,3,5,6-tetrachloro-4-trifluoromethyl-benzoyl chloride which is suitable as starting material in step b) may then be obtained by separating off the organic phase and evaporating it to dryness. If iodine has been added during the chlorination reaction, this is expediently removed before the separating off of the 2,3,5,6-tetra-chloro-4-trifluoromethyl-benzoyl chloride, for example, by addition of sodium bisulphite.

The fluorination in step (b) of the process according to the invention may be carried out, for example, using 5-20 mol of potassium fluoride per mol of 2,3,5,6-tetrachloro-4-trifluoromethyl-benzoyl chloride. This amount is preferably 6-10 mol. Small amounts of water-containing potassium fluoride may also be employed. In this case, it is advantageous to initially combine only the solvent and potassium fluoride and to remove the water by distilling a small amount of solvent together with the water. 1-5 times the amount by weight, preferably 1.5-5 times the amount by weight, relative to 2,3,5,6-tetrachloro-4-trifluoromethyl-benzoyl chloride, of solvent may be employed, for example. Step (b) of the process according to the invention may be carried out, for example, at temperatures from 150° to 200° C. Temperatures from 160° to 190° C. are preferred. Suitable reaction times at the preferred temperatures are, for example, those from 12 to 20 hours. A preferred solvent for this step is tetramethylene sulphone.

Steps (c) and (d) of the process according to the invention are preferably allowed to proceed immediately after one another, and to accomplish this, water, for example, in an equimolar amount or a molar excess, for example, 1.5 times the equimolar amount, in each case relative to the educt, is simply added to the entire reaction mixture present after step (b), preferably after cooling thereof to a temperature of 100° C. or less.

The decarboxylation (step (d) of the process according to the invention) generally starts at temperatures around 80° C., that is to say possibly during the addition of water. The decarboxylation is preferably carried out to completion at temperatures in the range from 100° to 160° C. (bottom temperature).

2,3,5,6-Tetrafluoro-benzotrifluoride formed may already be removed by distillation during the decarboxylation. This and all volatile components which pass over up to the boiling point of the solvent (for example, tetramethylene sulphone) are expediently collected together. Since the crude 2,3,5,6-tetrafluoro-benzotrifluoride obtained generally still contains water and tetramethylene sulphone, it is generally advantageous to wash it with a little water and subsequently to dry it.

In step (e) of the process according to the invention, 2,3,5,6-tetrafluoro-benzotrifluoride may be employed, for example, as it is produced by the work-up, described above, of the reaction mixture from step (d). The oleum may contain, for example, from 10 to 50% by weight of $SO_3$. It preferably contains 20 to 30% by weight of $SO_3$. The oleum may be employed, for example, in an amount from one mol or more of $SO_3$, relative to the product of step (d). Larger excesses of $SO_3$, for example, those of 4 times the molar amount or more, do not generally interfere, but are uneconomic. Suitable temperatures for carrying out step (e) are, for example, those from 70° to 120° C., and suitable reaction times are, for example, those from 2 to 5 hours.

The 2,3,5,6-tetrafluorobenzoic acid thus prepared may be isolated, for example, by stirring the reaction mixture, after cooling, into an ice-water mixture, filtering off the precipitate which forms, if appropriate washing with a little cold water, and drying.

In this fashion, 2,3,5,6-tetrafluoro-benzoic acid may be prepared in yields from, for example, 50-60% of theory (relative to 4-trifluoromethyl-benzoyl fluoride employed) and in purities of greater than 95%, frequently greater than 98%, whilst avoiding the disadvantages of the known processes. It is extremely surprising that the present invention makes available a process, for the preparation of 2,3,5,6-tetrafluoro-benzoic acid, which not only requires relatively easily accessible starting materials and reactions and chemicals which are relatively easy to handle, but also in which the desired product is obtained in relatively high yields and in excellent purity, since side reactions to a considerable extent were to be expected in the process according to the invention, which, in the simplest case, comprises 3 reaction steps. It was to be expected, for example, that the $CF_3$ group in step (a) would not behave so relatively inertly, but would co-react during the chlorination and/or work-up and undesired by-products would thereby be produced in considerable amounts. For example, $CF_2Cl$ and/or $CFCl_2$ group-containing by-products can be produced from $CF_3$ groups by chlorination. 2,3,5,6-tetrachloroterephthaloyl chloride can be produced by hydrolysis of $CF_3$ groups, and/or tri- and/or dichloro-4-trifluoromethylbenzoyl chloride can be produced by incomplete chlorination of the aromatic nucleus. It is furthermore surprising that a very pure 2,3,5,6-tetrafluorobenzoic acid can be isolated by carrying out the process according to the invention in a simple fashion, even when the intermediates which arise are not subjected to particular purification and by-products produced there are dragged along into step (e).

The present invention also relates to the hitherto unknown compound 2,3,5,6-tetrachloro-4-trifluoromethylbenzoyl chloride. This may be obtained by terminating the previously described process according to the invention after step (a), working up the reaction mixture as described there, and, if appropriate, purifying further.

2,3,5,6-Tetrachloro-4-trifluoromethyl-benzoyl chloride may be used as an intermediate for the advantageous preparation of 2,3,5,6-tetrafluoro-benzoic acid (see above), which is itself an intermediate for highly effective insecticides (see DE-OS (German Published Specification) No. 2,658,074).

The present invention furthermore relates to the previously unknown compound 2,3,5,6-tetrafluoro-4-trifluoromethyl-benzoyl fluoride. This may be obtained by terminating the previously described process according to the invention after step (b), and working up the reaction mixture, for example by distillation.

2,3,5,6-Tetrafluoro-4-trifluoromethyl-benzoyl fluoride may be used as an intermediate for the advantageous preparation of 2,3,5,6-tetrafluorobenzoic acid (see above), which is itself an intermediate for highly-effective insecticides (see DE-OS (German Published Specification)- No. 2,658,074).

EXAMPLES

Example 1

(a) 1 kg of carbon tetrachloride, 870 g of chlorosulphonic acid, 288 g of 4-trifluoromethyl-benzoyl fluoride and 6 g of iodine were placed in a 2 liter glass stirred vessel, and chlorine was passed into this mixture at a temperature of 55° to 60° C. After 700 g of chlorine had been passed in, the mixture was cooled to room temperature and stirred into a mixture of 2 kg of ice-water and 800 g of carbon tetrachloride with cooling, and aqueous sodium bisulphite solution was added until the iodine was removed (about 20 g of 40% strength solution).

The organic phase was then separated off, the aqueous phase was washed repeatedly with 200 g of fresh carbon tetrachloride, and the carbon tetrachloride was removed from the combined carbon tetrachloride extracts on a rotary evaporator. 505 g of 83% pure 2,3,5,6-tetrachloro-4-trifluoromethyl-benzoyl chloride having a melting point of 72° to 76° C. were thus obtained. This corresponds to a yield of pure product of 80.5% of theory.

(b) 1,680 g of tetramethylene sulphone and 600 g of standard commercial potassium fluoride were placed in a 2 liter glass stirred vessel which was fitted with a distillation attachment. Moisture contained in the potassium fluoride was removed by distillation of 40 g of tetramethylene sulphone. 505 g of the product obtained according to (a) were then added at 90° C. internal temperature, and the mixture was heated at 180° C. for 14 hours. The mixture was then cooled to 100° C., and 44 g of water were added dropwise. with the evolution of carbon dioxide starting. After completion of the addition of water, the mixture was stirred for 15 minutes, then slowly warmed to 160° C., at a not too vigorous carbon dioxide evolution rate, and the distillate passing over was collected. After completion of the carbon dioxide evolution, a vacuum was applied and the distillate passing over up to 140° C. at 20 mbar was collected. The combined distillates were washed with a little water, subsequently dried and redistilled. 216 g of up to 88% pure 2,3,5,6-tetrafluoro-benzotrifluoride having a boiling point of 112° C. were thus obtained. This corresponds to a yield of pure product of 72% of theory.

(c) 434 g of 20% strength oleum and 216 g of the product obtained according to (b) were mixed in a glass vessel and heated to the reflux temperature (103° C.) with stirring. When the reflux subsided, the internal temperature was increased slowly to 120° C. After 3 hours, the reaction mixture was cooled to 3° C., and 200 g of ice-water were stirred in with cooling, the temperature being kept below 30° C. The suspension forming was cooled to 3° C., and the precipitate was filtered off, washed with a little ice-water and dried. 166 g of 2,3,5,6-tetrafluoro-benzoic acid having a melting point of 148° C. were obtained, which corresponds to 97% of theory. The purity of the 2,3,5,6-tetrafluorobenzoic acid thus isolated was greater than 99%.

Example 2

The procedure as in Example 1 a) was followed, but the 2,3,5,6-tetrachloro-4-trifluoromethyl-benzoyl chloride thus obtained was purified still further, by recrystallizing it from a mixture of carbon tetrachloride and petroleum ether.

390 g of a 98% pure 2,3,5,6-tetrachloro-4-trifluoromethyl-benzoyl chloride having a melting point of 76° C. were thus obtained.

Example 3

The procedure as in Example 1 (b) was followed, but water was not added at 100° C. after the reaction with potassium fluoride, but instead the reaction mixture was distilled to 140° C. at 20 mbar and subsequently redistilled.

133 g of a 92% pure 2,3,5,6-tetrafluoro-4-trifluoromethyl-benzoyl fluoride having a boiling point of 54°–56° C./20 mbar were thus obtained.

Example 4

The procedure as in Example 1(a) was followed, but 1.1 kg of 1,1,2,2-tetrachloroethane were employed in place of carbon tetrachloride, and the chlorine was passed in at 45° to 50° C. 511 g of 95% pure 2,3,5,6-tetrachloro-4-trifluoromethylbenzoyl chloride having a melting point of 75°–76° C. were obtained. This corresponds to a yield of 92.5% of theory.

Example 5

The procedure as in Example 4 was followed, but 900 g of sulphuryl chloride were employed in place of tetrachloroethane. The result corresponded to Example 4.

It will be appreciated that the instant specification and claims are set forth by way of illustration and not limitation, and that various modifications and changes may be made without departing from the spirit and scope of the present invention.

What is claimed is:

1. A process for the preparation of 2,3,5,6-tetrafluorobenzoic acid comprising
   (a) chlorinating 4-trifluoromethyl-benzoyl fluoride in the presence of chlorosulphonic acid at temperatures of less than 60° C. to form 2,3,5,6-tetrachloro-4-trifluoromethyl-benzoyl chloride,
   (b) fluorinating the 2,3,5,6-tetrachloro-4-trifluoromethyl-benzoyl chloride using potassium fluoride in the presence of an aprotic, dipolar, inert solvent to form 2,3,5,6-tetrafluoro-4-trifluoromethyl-benzoyl fluoride,
   (c) hydrolyzing the 2,3,5,6-tetrafluoro-4-trifluoromethyl-benzoyl fluoride to form 2,3,5,6-tetrafluoro-4-trifluoromethyl-benzoic acid,
   (d) decarboxylating the 2,3,5,6-tetrafluoro-4-trifluoromethyl-benzoic acid at an elevated temperature to form 2,3,5,6-tetrafluoro-benzotrifluoride, and
   (e) saponifying the 2,3,5,6-tetrafluoro-benzotrifluoride using oleum to form 2,3,5,6-tetrafluoro-benzoic acid.

2. A process according to claim 1, further comprising conducting said chlorinating in the presence of a solvent.

3. A process according to claim 1, wherein the products of steps (b) and (c) are not isolated.

4. A process according to claim 1, wherein the steps (b), (c) and (d) are carried out immediately one after another in the same reaction vessel.

5. A process according to claim 1, wherein in step (a) the chlorosulphonic acid is present in an amount from 2 to 10 mol per mol of 4-trifluoromethyl-benzoyl fluoride and the chlorination is carried out in the presence of a solvent.

6. A process according to claim 1, wherein in step (a) the chlorosulphonic acid is present in an amount from 4 to 7.5 mol per mol of 4-trifluoromethyl-benzoyl fluoride and the chlorination is carried out in the presence of a solvent.

7. A process according to claim 1, wherein the chlorinating is carried out using elemental chlorine.

8. A process according to claim 7, further comprising adding 0.01 to 2% by weight iodine relative to the chlorine.

9. A process according to claim 1, wherein the chlorinating is conducted at a temperature of 40° to 60° C.

10. A process according to claim 1, wherein the chlorinating is conducted at a temperature of 40° to 55° C.

11. A process according to claim 1, wherein 5 to 20 mol of potassium fluoride are employed per mol of 2,3,5,6-tetrachloro-4-trifluoromethyl-benzoyl chloride in step (b).

12. A process according to claim 1, wherein 6 to 10 mol of potassium fluoride are employed per mol of 2,3,5,6-tetrachloro-4-trifluoromethyl-benzoyl chloride in step (b).

13. A process according to claim 1, wherein the fluorinating is conducted at a temperature of 150° to 200° C.

14. A process according to claim 1, wherein the fluorinating is conducted at a temperature of 160° to 190° C.

15. A process according to claim 1, wherein water is used for the hydrolyzing and from 1 to 1.5 mol of water, relative to the 2,3,5,6-tetrafluoro-4-trifluoromethyl-benzoyl fluoride are employed in step (c).

16. A process according to claim 1, wherein the hydrolyzing is conducted at a temperature of 100° C. or less.

17. A process according to claim 1, wherein step (d) is continued to completion at a temperature of 100° to 160° C.

18. A process according to claim 1, wherein in step (e), oleum, containing from 10 to 50% by weight of $SO_3$, is employed in an amount of 1 mol or more, relative to the 2,3,5,6-tetrafluoro-benzotrifluoride, and the saponifying is carried out at a temperature of 70° to 120° C.

19. 2,3,5,6-Tetrachloro-4-trifluoromethyl-benzoyl fluoride.

20. 2,3,5,6-Tetrafluoro-4-trifluoromethyl-benzoyl fluoride.

* * * * *